United States Patent [19]

Glassman

[11] 4,072,150
[45] Feb. 7, 1978

[54] DOUBLE-DUTY DIAPER AND INSERT THEREFOR

[76] Inventor: Jacob A. Glassman, 1680 Michigan Ave., Miami Beach, Fla. 33139

[21] Appl. No.: 741,949

[22] Filed: Nov. 15, 1976

[51] Int. Cl.$^2$ .......................................... A61F 13/16
[52] U.S. Cl. .................................. 128/284; 128/287; 128/290 R
[58] Field of Search .......... 128/290 R, 290 H, 290 W, 128/284, 287, 268, 295

[56] References Cited

U.S. PATENT DOCUMENTS

| 2,952,259 | 9/1960 | Burgeni | 128/290 R |
| 3,000,381 | 9/1961 | Mulhole et al. | 128/287 X |
| 3,049,124 | 8/1962 | Thompson | 128/287 |
| 3,926,189 | 12/1975 | Taylor | 128/290 R X |

FOREIGN PATENT DOCUMENTS

| 6,415,093 | 6/1965 | Netherlands | 128/290 R |

Primary Examiner—Robert W. Michell
Assistant Examiner—Michael H. Thaler
Attorney, Agent, or Firm—Elmer L. Zwickel

[57] ABSTRACT

A double-duty diaper characterized by the inclusion of a moisture absorbent auxiliary insert strip to absorb moisture and fabricated to facilitate easy folding of the strip while the diaper is being worn so as to cover any solids prior to removing the strip from the main diaper. The strip also insures wide distribution of moisture and resists premature spill-over.

16 Claims, 8 Drawing Figures

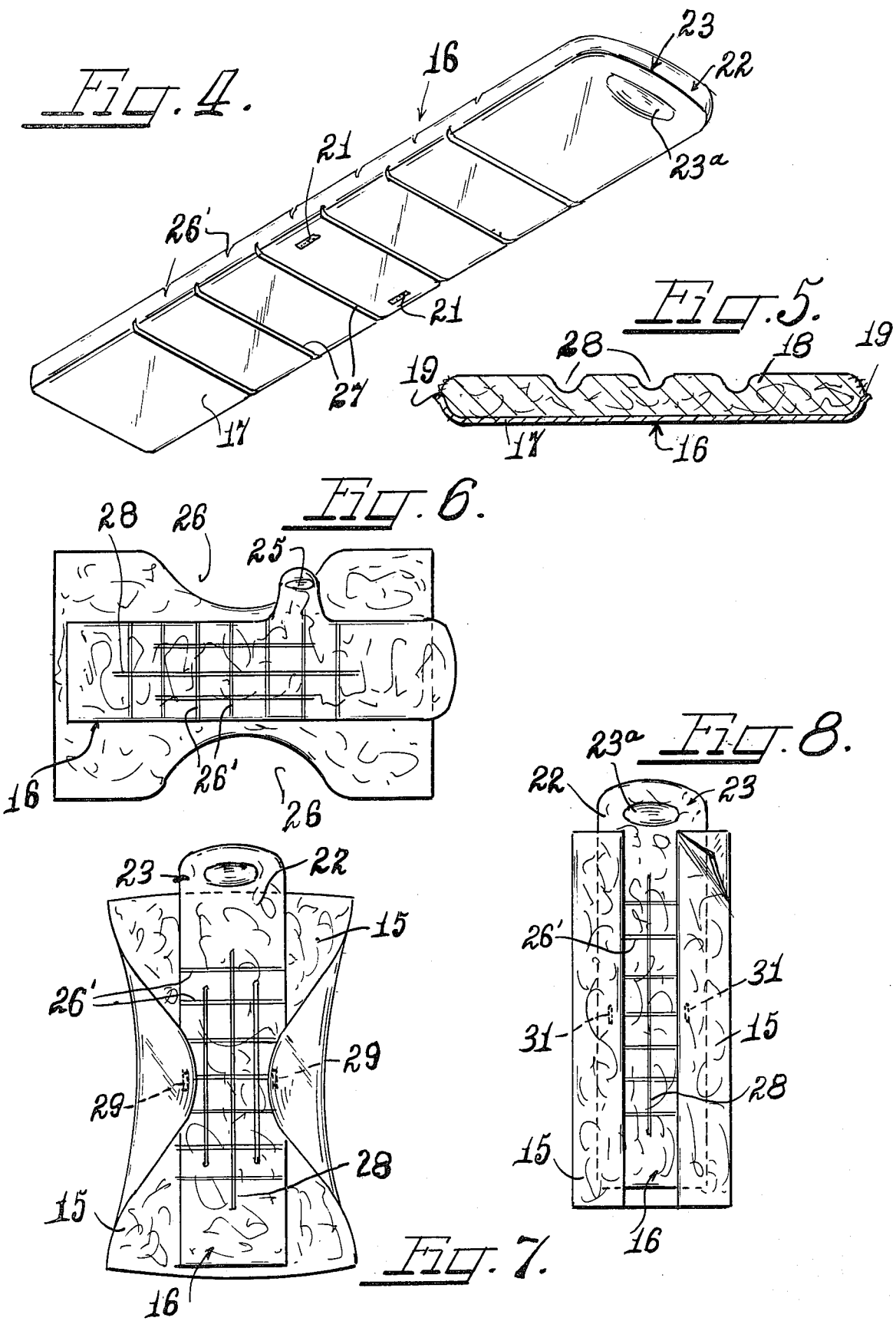

DOUBLE-DUTY DIAPER AND INSERT THEREFOR

The invention relates to improvements in disposable double-duty diapers and to auxiliary insert strips therefor. The strip also embodies a novel method of fabrication. The main diaper and insert strip are each formed of one or more layers of highly absorbent material overlying a layer of moisture impervious material and the insert is arranged over the longitudinal central area of the main diaper and is constructed so that, when soiled or wetted, it may be partially rolled over to cover the soiled or wetted area thereof and be then withdrawn from the main diaper without removing the main diaper from the body of the wearer, thus leaving the retained main diaper relatively clean and dry for further use.

The auxiliary insert strip is further characterized by having its perimeter edges sealed to prevent or retard spill-over of moisture from the insert strip onto the absorbent material of the main diaper. Further, manual access to the auxiliary insert strip is facilitated by providing the strip with a pull tab or handle portion, which may or may not be reinforced to resist rupture when a pulling force is applied thereto. Preferably, the auxiliary insert strip is provided on one or both of its faces with longitudinally spaced lateral recesses or channels designed to facilitate folding or rolling of a soiled insert and one face is also formed with one or more longitudinal grooves or channels to assist widespread distribution of moisture.

The foregoing general recitation of the main characteristics of the insert strip tend to distinquish the disclosed structure from those shown in my co-pending applications Ser. No. 592,406 now U.S. Pat. No. 4,019,517 and Ser. No. 603,442 now U.S. Pat. No. 4,022,210, as well as from the teachings in Jespersen U.S. Pat. No. 3,595,235, dated July 27, 1971, particularly in the ready separation of the auxiliary insert strip from the main diaper and in the specifics of the insert strip, none of which are shown or suggested in Jespersen. The present teaching of the insert strip structure is also clearly different patentwise from the showning of the plain insert strip secured in place by snap fasteners, disclosed in Salk U.S. Pat. No. 3,162,196, dated Dec. 22, 1964, or in the Margraf U.S. Pat. No. 3,050,063, dated Aug. 21, 1962. Neither one of these patents teach, for example, the lateral folding assisting grooves, the sealing of the insert edges, fluid distribution grooves, or the readily available reinforced pull tab or handle.

It is therefore a feature of the invention to provide a novelly constructed double-duty diaper which obviates the need to replace a wetted or soiled diaper at frequent intervals. Such proceedure is annoying not only to the wearer but also to the attendant who must change the diaper. By fitting the main diaper with a readily removable centrally located auxiliary inner absorbent layer of considerably less width than that of the main diaper, but of a length that locates one end bearing a hand-hold grip position to be readily grasped for pulling out the insert strip and which is formed in a manner to facilitate its being folded or rolled to cover any solids deposited on the insert strip so as to prevent body soilage.

An object of the invention is therefore to provide an insert strip for a disposable double-duty diaper embodying the characteristics recited hereinabove.

Another object is to provide an insert strip of the character recited with a novel reinforced pull handle on at least one edge.

Another object is to seal the perimeter edges of the insert strip so as to minimize spill-over onto the main diaper with which it is associated.

Another object it to fabricate the insert strip in such manner as to facilitate its being rolled or folded in whole or in part prior to removal from the main diaper with which it is associated.

Another object is to provide a novel method fabrication of a double-duty diaper and a removable insert therefore.

Other objects and advantages of the invention will become apparent with reference to the following description and accompanying drawings:

IN THE DRAWINGS

FIG. 4 is a perspective view of the auxiliary insert strip, viewed from the bottom side.

FIG. 5 is a lateral sectional view of the auxiliary insert strip.

FIG. 6 is a plan view of a double-duty diaper having recessed side edges, and an insert strip having a hand hold tab on its side edge.

FIG. 7 is a plan view of a double-duty diaper having the central area of the side portions on the main diaper adhesively tacked over the insert strip.

FIG. 8 is a view similar to FIG. 7, showing the side margins of the main diaper fan-folded to overly the side margins of the insert strip, to which it is adhesively tacked.

Referring to the disclosures in the accompanying drawings, there is disclosed a number of modifications all of which are basically similar.

Figure 1:
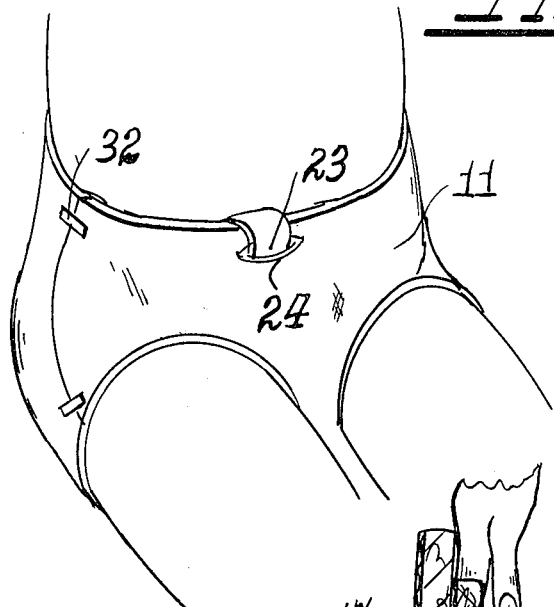
FIG. 1 is a perspective view of the double-duty diaper arranged on a human body.
Figure 2:
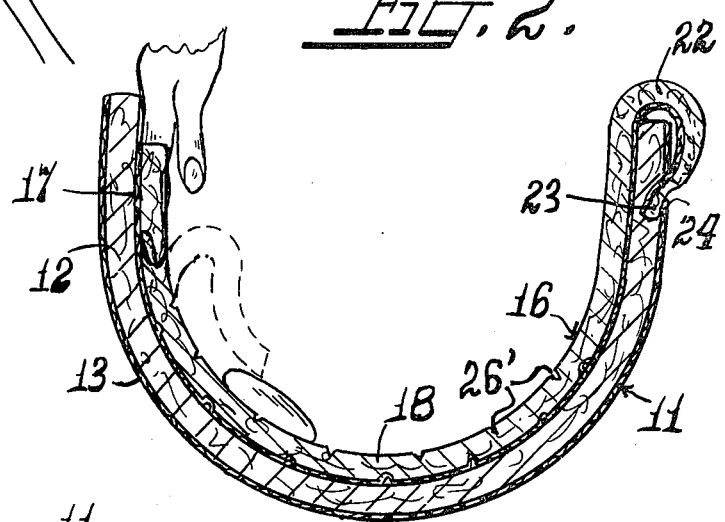
FIG. 2 is a longitudinal sectional view of the double-duty diaper.
Figure 3:
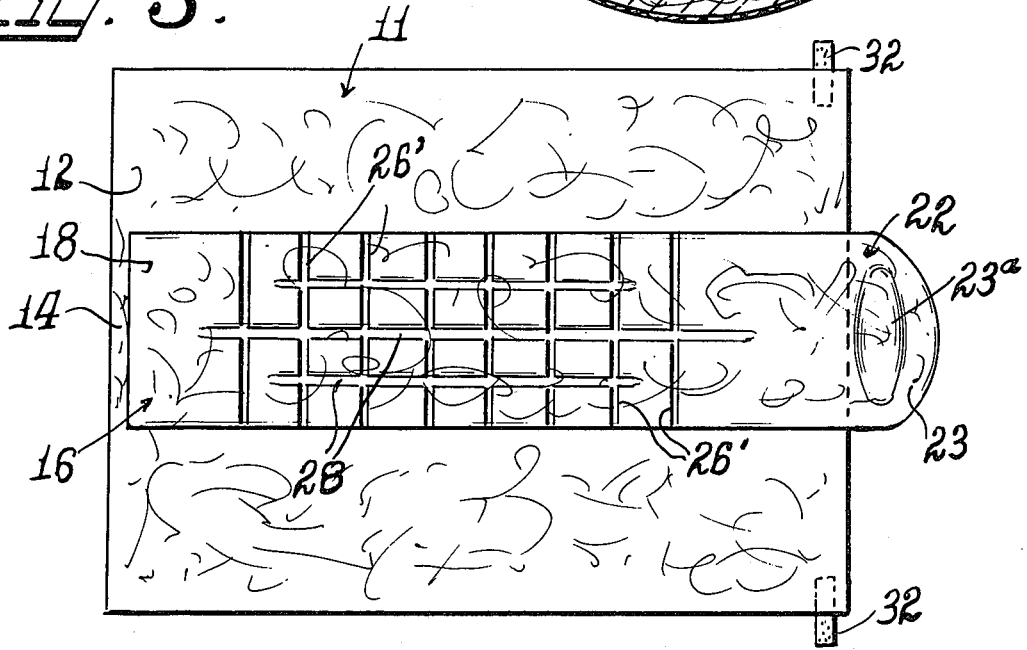
FIG. 3 is a plan view of the body contacting surface of one embodiment of the double-duty diaper.

More specifically, upon reference to the teachings in FIGS. 1 through 5, the double-duty diaper includes a main diaper 11 comprised of a thick layer of highly moisture absorbent material 12, such as cotton, cellulose, crim or the like, having a thin outside layer or backing sheet 13 of moisture impervious material. These two layers are of like size and have preferably a rectangular shape and preferably are secured together along their complemental edges thus to form a substantially rectangular main diaper having a longitudinal central portion or area 14 and adjacent side marginal areas 15.

An auxiliary insert strip 16 comprised of a bottom layer 17 of moisture impervious material, and at least one thick layer 18 of highly moisture absorbent material, such as cotton, cellulose, crim or the like. These two layers are secured together along complemental edges, as at 19, to form a unitary strip and present means to prevent moisture spill-over at said edges. The insert strip is laid over the central portion 14 of the main diaper and may be detachably tacked thereto by a rupturable adhesive 21. The insert strip 16 preferably has a length slightly greater than that of the longitudinal central portion of the main diaper. In any event, when the insert strip is in place on the central portion of the main diaper, at least one end 22 of the strip extends beyond one end edge of the main diaper to provide a tab 23 that can be grasped between the fingers when removal of the insert strip is advisable. Preferably, the tab 23 is reinforced by fusing or adhesive in an area 23a to prevent its being inadvertently torn from the strip. Further, a slot 24 may be provided in the main diaper, in the region of the tab, to receive the tab tucked thereinto. In the alternative, a tab may be provided on one longitudinal edge of the insert strip, as illustrated at 25 in FIG. 6, which can be grasped by the fingers to facilitate sidewise removal of the strip. In this latter instance, the side edges of the main diaper may be recessed centrally of their length, as at 26 in FIG. 6, to afford ready access to the tab 25 and at the same time insure that when the diaper is being worn there will be but a minimum amount of sidewise compression between the wearer's thighs, thus eliminating bulging, wrinkling and/or gapping.

The insert strip 16 is formed preferably on both faces with lateral grooves 26', 27, which function to allow an attendant to insert one or more fingers between the main diaper 11 and the insert strip 16 and to then progressively fold or roll the insert strip (FIG. 2) sufficiently to carry the folded end portion into position overlying any solid waste or feces, whereupon the insert strip can be withdrawn without undue soiling of the body.

When the insert strip is wetted excessively, there would be a tendency for the excess moisture to spill over onto the main diaper prior to complete absorption by the strip. Now, to insure adequate distribution of moisture throughout the length of the insert strip, said strip is provided, in the absorbent surface facing the human body, with one or more longitudinal grooves or channels 28 that preferably terminate short of the strip ends. Also, the sealing of the perimeter edges 19 of the insert strip prevents moisture from seeping out of the edges and into the main diaper.

Referring to FIG. 7, the side margins 15 of the main diaper have their longitudinal central areas carried inwardly toward each other, which areas are lightly secured by adhesive 29 to the underlying insert sheet 16. In FIG. 8, the side margins 15 of the main diaper are fan-folded and secured folded by rupturable adhesive spots 31.

In use, the diaper, with the insert strip 16 in place on the longitudinal central portion of the main diaper, is fitted onto the wearer and may be secured by pins or by means of adhesive tabs 32. When the absorbent layer 18 of the insert strip 16 becomes wetted or soiled, the attendant may fold a portion of the strip over the soilded area and then grasp the exposed pull tab 23 or 25 of said strip and by the application of a slight tug can separate said insert strip from the main diaper 11 and withdraw said strip. As a consequence, the clean unsoiled or non-wetted main diaper remains in place and in effect constitutes a clean diaper. Thus, the diaper is in effect a double-duty diaper, the need to change frequently is cut in half and the wearer is undisturbed by the withdrawal of the insert strip. This is particularly advantageous when the wearer is sleeping.

Although I have described preferred embodiments of the invention in considerable detail, it will be understood that the description thereof is intended to be illustrative rather than restrictive, as details of the structure and method of fabrication may be modified or changed without departing from the spirit or scope of the invention.

I claim:

1. A double-duty diaper comprising, in combination, a main diaper including at least one relatively thick substantially rectangular layer of highly moisture absorbent material having a longitudinal central portion, an insert strip of less width than the main diaper also of highly moisture absorbent material super-imposed on said longitudinal central portion, a thin layer of moisture impervious material underlying the absorbent material of the insert strip, means lightly adhering the insert strip to the inner surface of said one layer, means embodied in the insert strip to facilitate at least one end thereof to be folded inwardly to overly an adjacent portion of said insert strip, and means for removing said insert strip from the main diaper without corresponding removal of or impairment of the diapering potential of said main diaper comprising the said insert strip having a size such that at least a portion thereof extends as a pull tab beyond a related edge of the main diaper.

2. The double-duty diaper recited in claim 1, wherein the insert strip is moisture sealed along all its edges.

3. The disposable double-duty diaper recited in claim 1, wherein means is provided to secure the main diaper about the waist portion of a human body with the insert strip in position to contact the body.

4. The double-duty diaper recited in claim 1, wherein the pull tab is reinforced to resist tearing.

5. The double-duty diaper recited in claim 1, wherein the pull tab extends beyond one longitudinal side edge of the main diaper.

6. The double-duty diaper recited in claim 1, wherein the pull tab extends beyond one end edge of the main diaper.

7. The double-duty diaper recited in claim 6, wherein the main diaper has a pocket to receive the pull tab.

8. The double-duty diaper recited in claim 6, wherein the insert strip has a series of lateral grooves on the side facing the main diaper to facilitate its being folded.

9. The double-duty diaper recited in claim 8, wherein the insert strip has a series of lateral grooves on the side facing the wearer to facilitate its being folded.

10. The double-duty diaper recited in claim 9, wherein the insert strip has a series of longitudinal grooves on its wearer facing surface to facilitate distribution of moisture.

11. The double-duty diaper recited in claim 10, wherein the side edges of the main diaper forming layer of moisture absorbent material each has a recess provided in its midlength portion to cause narrowing thereof in said midlength portion, and said insert strip has a width not greater than the width of the recessed midlength portion of the main diaper.

12. The double-duty diaper recited in claim 10, wherein the insert strip overlies substantially the longitudinal central portion of the main diaper and the side margins of the main diaper are folded over and adhesively tacked to the said insert strip prior to use.

13. The method of fabricating a double-duty diaper comprising the steps of superimposing on the body contacting surface of a thick layer of highly moisture absorbent material providing a main diaper having a longitudinal central portion, an insert strip including a layer of highly moisture absorbent material and a layer of moisture impervious material, both of less width than the said thick layer, sealing the perimeter edges of the strip to resist moisture spill-over, positioning said insert strip on said central portion with respect to said main diaper forming layer so that at least a portion of the insert strip projects beyond a related edge of said thick layer, thereby to provide a pull tab enabling withdrawal of the insert strip upon wetting or soiling thereof from said main diaper forming layer.

14. The method recited in claim 13, with the added step of forming lateral grooves in the insert strip to facilitate its being folded.

15. The method recited in claim 14, with the added step of forming longitudinal grooves in the exposed surface of the absorbent material of the insert strip to facilitate moisture distribution.

16. The method recited in claim 13, with the added step of forming longitudinal grooves in the longitudinal central portion of the insert strip.

* * * * *